United States Patent
Wald et al.

(10) Patent No.: US 10,261,145 B2
(45) Date of Patent: Apr. 16, 2019

(54) SYSTEM AND METHOD FOR IMPROVED RADIO-FREQUENCY DETECTION OR B0 FIELD SHIMMING IN MAGNETIC RESONANCE IMAGING

(71) Applicants: Lawrence Wald, Cambridge, MA (US); Jason Stockmann, Cambridge, MA (US)

(72) Inventors: Lawrence Wald, Cambridge, MA (US); Jason Stockmann, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 733 days.

(21) Appl. No.: 14/648,485

(22) PCT Filed: Dec. 2, 2013

(86) PCT No.: PCT/US2013/072591
§ 371 (c)(1),
(2) Date: May 29, 2015

(87) PCT Pub. No.: WO2014/088941
PCT Pub. Date: Jun. 12, 2014

(65) Prior Publication Data
US 2015/0323628 A1    Nov. 12, 2015

Related U.S. Application Data

(60) Provisional application No. 61/734,582, filed on Dec. 7, 2012.

(51) Int. Cl.
*G01V 3/00*    (2006.01)
*G01R 33/3415*    (2006.01)
(Continued)

(52) U.S. Cl.
CPC ....... *G01R 33/3415* (2013.01); *G01R 33/341* (2013.01); *G01R 33/3875* (2013.01); *A61B 5/055* (2013.01)

(58) Field of Classification Search
CPC .............. G01R 33/34; G01R 33/34007; G01R 33/341; G01R 33/3415; G01R 33/34084;
(Continued)

(56) References Cited

U.S. PATENT DOCUMENTS 9,439,735 B2 *  9/2016  Guttman ................ A61B 34/20
2003/0073898 A1 *  4/2003  Weiss ....................... A61B 5/06
                                                                600/410
(Continued)

FOREIGN PATENT DOCUMENTS

WO    2011/122084 A1    10/2011

OTHER PUBLICATIONS

International Search Report and Written Opinion dated Apr. 14, 2014, in connection with PCT/US2013/072591.

*Primary Examiner* — Thang X Le
(74) *Attorney, Agent, or Firm* — Quarles & Brady LLP (57) ABSTRACT

A system and method for magnetic resonance imaging (MRI) and static field (B0) shimming. A coil system includes a conductive loop configured to be arranged proximate to a region of interest (ROI). The coil system also includes an alternating current (AC) circuit electrically connecting the conductive loop to an AC electrical connection configured to be coupled to an MRI system to communicate medical imaging signals received by the conductive loop from the ROI during a medical imaging procedure to the MRI system. The coil system further includes a direct current (DC) circuit electrically connecting the conductive loop to a DC electrical connection configured to be coupled to a DC power source and a plurality of circuit components configured to
(Continued)

block DC signals from reaching the AC electrical connection in order to produce a spatially varying static magnetic field for shimming inhomogenieties of the static field.

19 Claims, 7 Drawing Sheets

(51) Int. Cl.
  *G01R 33/341* (2006.01)
  *G01R 33/3875* (2006.01)
  *A61B 5/055* (2006.01)
(58) Field of Classification Search
  CPC ............ G01R 33/3635; G01R 33/3628; G01R 33/3875; G01R 33/48; G01R 33/4818; G01R 33/481; G01R 33/4824; G01R 33/446; G01R 33/4835; G01R 33/4828; G01R 33/54; G01R 33/543; G01R 33/561; G01R 33/563; G01R 33/565; G01R 33/5611; G01R 33/5612; G01R 33/583; G01R 33/5659; G01R 33/56518; G01R 33/56536; G01R 33/56572; G01R 33/5614; G01R 33/5616; G01R 33/56509; G01R 33/385; G01R 33/56358; A61B 5/055; A61B 5/0555; A61B 5/7278; A61B 5/725

See application file for complete search history.

(56) References Cited

U.S. PATENT DOCUMENTS

| | | | |
|---|---|---|---|
| 2006/0273798 A1* | 12/2006 | Klieger .............. | G01R 33/3415 324/318 |
| 2007/0073140 A1* | 3/2007 | Fisher .................... | A61B 5/055 600/410 |
| 2007/0106170 A1 | 5/2007 | Dunseath, Jr. et al. | |
| 2008/0007250 A1* | 1/2008 | Wiggins ................. | A61B 5/055 324/200 |
| 2010/0039113 A1* | 2/2010 | Vartiovaara ........ | G01R 33/3657 324/322 |
| 2012/0139541 A1* | 6/2012 | Weiss ................... | G01R 33/583 324/318 |
| 2012/0161767 A1* | 6/2012 | Hardy ................ | G01R 33/3642 324/318 |
| 2013/0207655 A1* | 8/2013 | Biber ................... | G01R 33/341 324/321 |
| 2014/0002084 A1 | 1/2014 | Han et al. | |
| 2015/0177344 A1* | 6/2015 | Han ................... | G01R 33/3628 324/322 |

* cited by examiner

SYSTEM AND METHOD FOR IMPROVED RADIO-FREQUENCY DETECTION OR B0 FIELD SHIMMING IN MAGNETIC RESONANCE IMAGING

CROSS-REFERENCE TO RELATED APPLICATIONS

This application represents the national stage entry of PCT International Application No. PCT/US2013/072591 filed Dec. 2, 2013, which claims priority to, U.S. Provisional Patent Application No. 61/734,582 filed on Dec. 7, 2012, the disclosures of which are incorporated by reference here in their entirety for all purposes.

STATEMENT REGARDING FEDERALLY SPONSORED RESEARCH

N/A

BACKGROUND OF THE INVENTION

The field of the invention is magnetic resonance imaging (MRI) and systems. More particularly, the invention relates to a system including and method for using an improved MRI coil design that can be used to improve radio frequency (RF) detection and/or $B_0$ field shimming.

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

Spatial variation in the static background field ($B_0$) commonly occurs in areas about the head and body, where tissue magnetic susceptibility changes abruptly, which distorts the $B_0$ field lines and creates off-resonance signals. Perturbation of the $B_0$ field can cause image artifacts, such as geometric distortion and signal loss due to intravoxel dephasing, particularly at high field strengths, such as 3 Tesla and 7 Tesla. This field inhomogeneity remains an obstacle to applications such as functional MRI (fMRI) of the brain with echo planar imaging (EPI) sequences, which rely on long echo trains that are sensitive to off-resonance effects. Artifacts are particularly pronounced in brain areas near the sinus cavities, which suffer from strong $B_0$ inhomogeneity caused by the air-filled sinus cavities in close proximity to the tissue being imaged. A common way to partially overcome this obstacle is to reduce the echo train length with parallel imaging methods, such as GRAPPA, but this comes at the expense of signal-to-noise ratio by reducing the accuracy of the fMRI measurement.

In conventional MRI scanners, inhomogeneity is compensated for using body-sized shim coils inside the bore to generate first and second-order spherical harmonic fields. Unfortunately, these solutions are ill suited to match (and cancel) the rapid variation of the $B_0$ field in the head, particularly in the sinus regions, because such solutions generate fields that are spatially slowly-varying. Recently, arrays of multiple loop coils placed in the vicinity of the head have been used to generate higher-order field shapes, providing more accurate compensation of $B_0$ inhomogeneity in mice (Juchem C, Brown P B, Nixon T W, McIntyre S, Rothman D L, de Graaf R A. Multicoil shimming of the mouse brain. Magn Reson Med. 66(3); 2011:893-900.) and humans (Juchem C, Nixon T W, McIntyre S, Boer V O, Rothman D L, de Graaf R A. Dynamic multi-coil shimming of the human brain at 7 T. J Magn Reson. 212(2); 2011: 280-8.). As described by Juchem, et al., field maps of each loop are obtained and each element is driven with the necessary amount of direct current to shim out the $B_0$ inhomogeneity in the sample. In this approach, RF transmit and/or receive coils are nested inside an array of 32 or more DC shim coils. Unfortunately, placing shim coils inside the RF coils leads to excessive shielding and interaction with the shim coils and loss of RF transmit field and/or receive sensitivity. Also, the presence of separate shim loops consumes space and limits the number of RF receive coils that can be placed close to the body, in addition to reducing the SNR of these coils.

Therefore, it would be desirable to have a system and method to shim or compensate for $B_0$ inhomogeneities, such as are common about the head and elsewhere, that does not limit the pulse sequences available for imaging or undesirably shield the RF fields employed and result in loss of RF detection sensitivity or transmit efficiency.

SUMMARY OF THE INVENTION

The present invention overcomes the aforementioned drawbacks by providing a system and method for shimming $B_0$ field inhomogeneities without the substantial limitations of traditional methods. The present invention permits simultaneous $B_0$ field shimming and increased RF field sensitivity by providing a head coil system formed of an array of loop coils that are shared to achieve both purposes; shimming and RF detection and/or generation. Instead of separating the shim and RF coil functions to allow the shim coil to use many turns of wire and increase the inductance (and, thus, field per unit current), the present invention increases efficiency by bringing the shim coils closer to the subject being imaged, such as the head of a subject. The loop structures serve as both RF detectors and $B_0$ shim coils by sharing a conductor for both the RF signal and DC current. In this way, space is conserved in the region around the subject being imaged. The DC current amplitude can be switched during the imaging examination to allow a "slice-by-slice" optimization of the B0 field.

In accordance with one aspect of the invention, a coil system configured to be utilized with a magnetic resonance imaging (MRI) system to acquire medical imaging data from a subject during a medical imaging procedure is disclosed that includes a conductive loop configured to be arranged proximate to a region of interest (ROI) of the subject during the medical imaging procedure. The coil system also includes an alternating current (AC) circuit electrically connecting the conductive loop to an AC electrical connection configured to be coupled to the MRI system to communicate medical imaging signals received by the conductive loop from the ROI during the medical imaging procedure to the MRI system. The coil system further includes a direct current (DC) circuit electrically connecting the conductive loop to a DC electrical connection configured to be coupled to a DC power source and a plurality of circuit components configured to block DC signals from reaching the AC electrical connection.

In accordance with another aspect of the invention, a magnetic resonance imaging (MRI) system is disclosed that includes a magnet system configured to generate a static magnetic field about at least a region of interest (ROI) of a subject arranged in the MRI system and plurality of gradient coils configured to establish at least one magnetic gradient field with respect to the static magnetic field. The MRI system also includes a radio frequency (RF) system that includes a RF signal input configured to deliver medical imaging signals acquired by the RF system during a medical imaging process conducted with the MRI system to the MRI system and an RF antenna configured to be arranged proximate to the ROI of the subject. The RF system also includes an alternating current (AC) circuit electrically connecting the RF antenna to the RF signal input to communicate the medical imaging signals received by the RF antenna from the ROI during the medical imaging process to the MRI system and a direct current (DC) circuit electrically connecting the RF antenna to a DC electrical connection. The MRI system includes a power source coupled to the DC electrical connection of the DC circuit to deliver DC power to the RF antenna to generate a shimming magnetic field using the RF antenna to compensate for inhomogeneities of the static magnetic field generated by the magnet system.

In accordance with yet another aspect of the invention, a method for performing a medical imaging procedure using a magnetic resonance imaging (MRI) system is disclosed that includes arranging a subject within the MRI system and positioning at least one external imaging coil to acquire image data from the subject using at least one RF antenna. The method also includes coupling the at least one RF antenna to an RF input of the MRI system to deliver the image data to the MRI system, coupling the at least one RF antenna to a direct current (DC) power source, and determining a position of magnetic field inhomogeneities in a static magnetic field of the MRI system with respect to the subject. The method further includes determining a shimming field configured to compensate for the magnetic field inhomogeneities, delivering a DC power from the DC power source to the at least one RF antenna configured to at least partially compensate for the magnetic field inhomogeneities, and acquiring image data form the subject using the at least one RF antenna while at least partially compensating for the magnetic field inhomogeneities using the RF antenna.

The foregoing and other advantages of the invention will appear from the following description.

DETAILED DESCRIPTION OF THE PREFERRED EMBODIMENT

Figure 1:
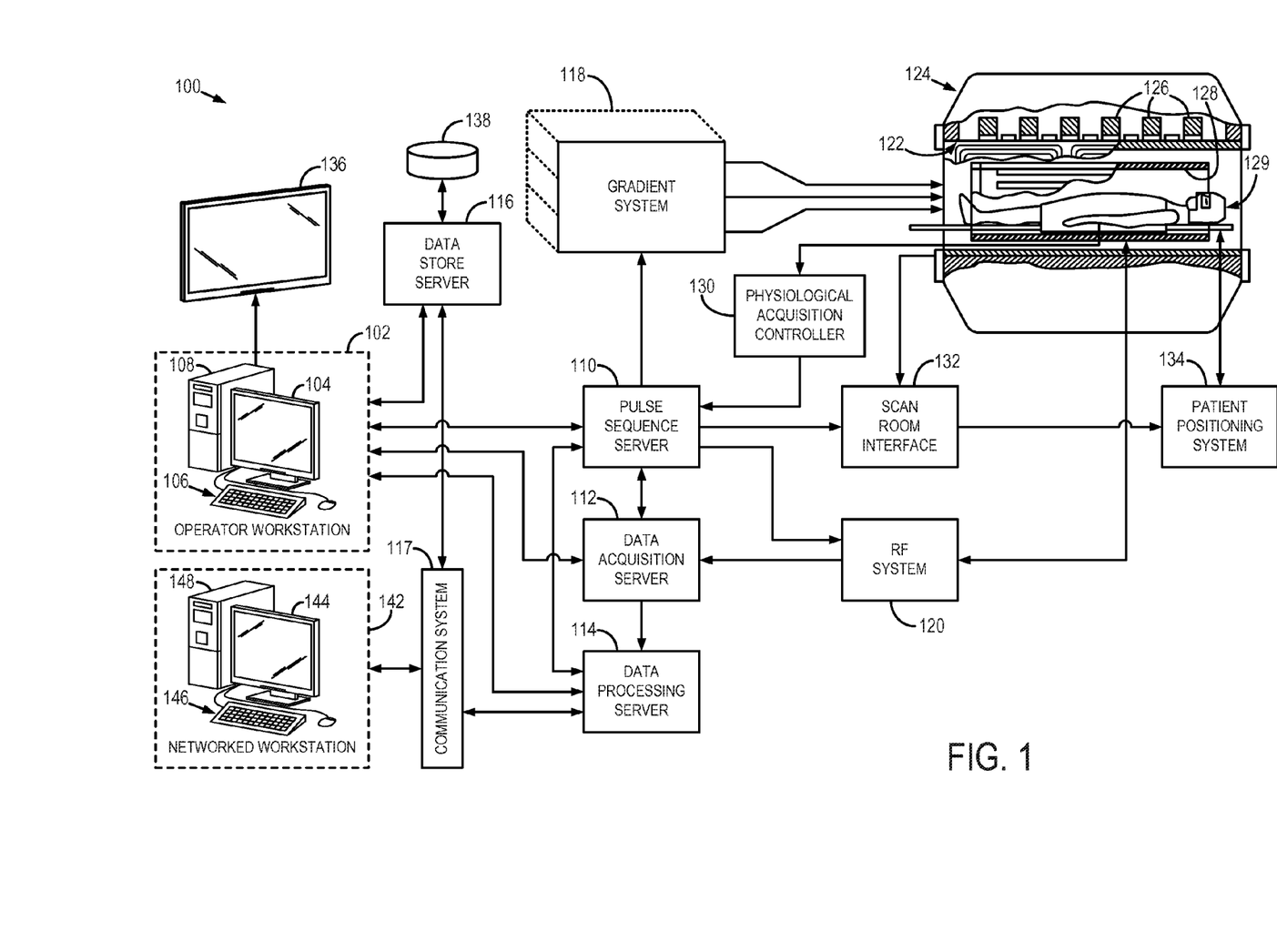
FIG. 1 is a block diagram of an MRI system which employs the present invention.

Referring particularly now to FIG. 1, an example of a magnetic resonance imaging (MRI) system 100 is illustrated. The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128 and/or local coil, such as a head coil 129.

RF waveforms are applied by the RF system 120 to the RF coil 128, or a separate local coil, such as the head coil 129, in order to perform the prescribed magnetic resonance pulse sequence. Responsive magnetic resonance signals detected by the RF coil 128, or a separate local coil, such as the head coil 129, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays, such as the head coil 129.

The RF system 120 also includes one or more RF receiver channels. Each RF receiver channel includes an RF preamplifier that amplifies the magnetic resonance signal received by the coil 128/129 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Figure 2:
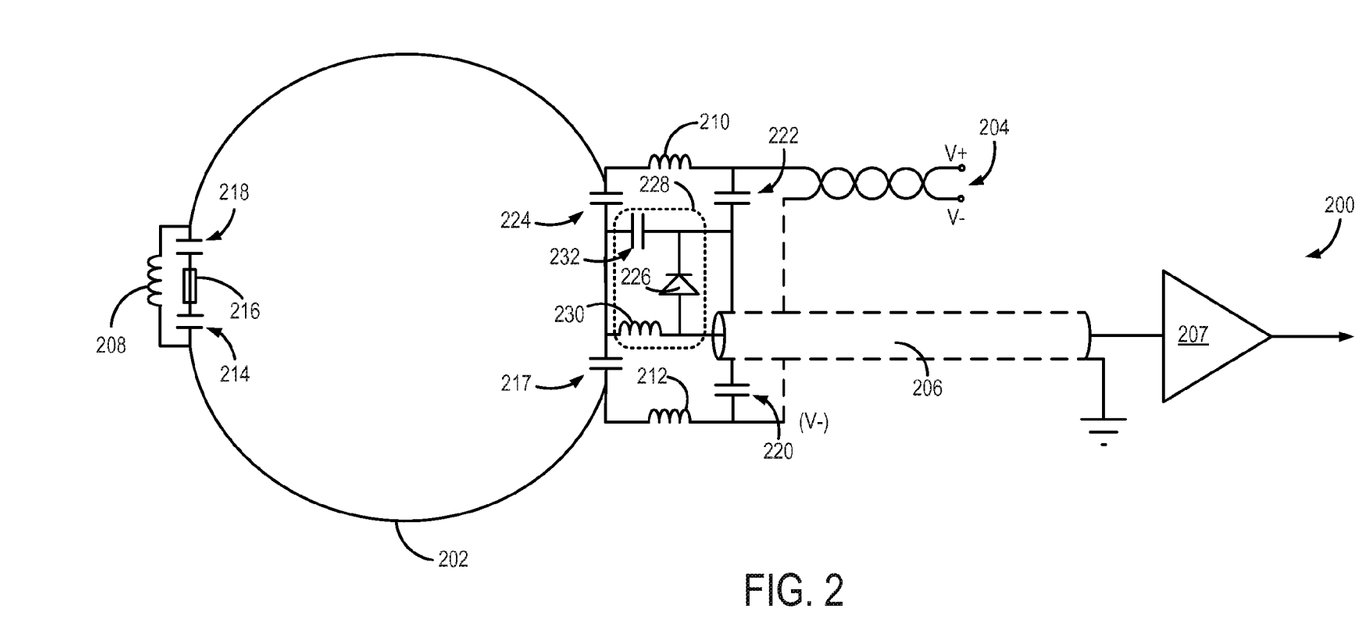
FIG. 2 is a schematic circuit diagram of an RF coil system in accordance with the present invention.

Referring to FIG. 2, the local coil system 129 of FIG. 1 may be a multi-coil RF array adapted to carry DC by bridging RF tuning and matching capacitors with inductors. Alternatively, the DC current carrying structure may be a separate wire adjacent to the RF carrying wire with filters or inductors in the DC loop to block the induction of unwanted RF currents on the DC structure. Specifically, referring to FIG. 2, an AC/DC coil system 200 is provided that includes a conductive loop or antenna 202. As illustrated, the conductive loop 202 may be formed as a single loop or more than one turn of loop conductor. The AC/DC coil system 200 is connected to a DC electrical connection 204, which may take the form of a twisted pair, for communication of DC signals and connected to a an alternating current (AC) electrical connection 206, which may take the form of a coaxial cable. The AC electrical connection 206 may be connected through, for example, a pre-amplifier 207 for communication of AC or medical imaging signals to the MRI system of FIG. 1. Thus, shim currents floe on the same conductive loop 202 as the RF signals.

A plurality of circuit components, such as inductive chokes 208, 210, 212 are connected to the conductive loop 202. One inductive choke 208 forms a direct current (DC) bridge across an RF tuning capacitor 214 and a fuse 216. Another inductive choke 212 forms a bridge across another tuning capacitor 217. In operation, the inductors 208, 210, 212 act as open circuits at RF or AC signals, but act as closed circuits permitting unencumbered flow of the DC signals.

Additional inductive chokes (not shown) or filter circuits may be optionally included to prevent RF signals from straying onto the twisted pair 204 used to supply the DC signals.

A plurality of circuit components, such as blocking capacitors 218, 220, 222, 224 are designed to pass RF signals and block DC signals. A diode 226 is connected to the coaxial cable 206 to create an LC resonance circuit 228 between an inductor 230 in series with the diode 226 and a matching capacitor 232 to detune the coil 202 during RF transmission. The diode 226 also protects the pre-amplifier 207 during RF transmission. The matching capacitor 234 couples the coil 202 to the circuit components.

Figure 3:
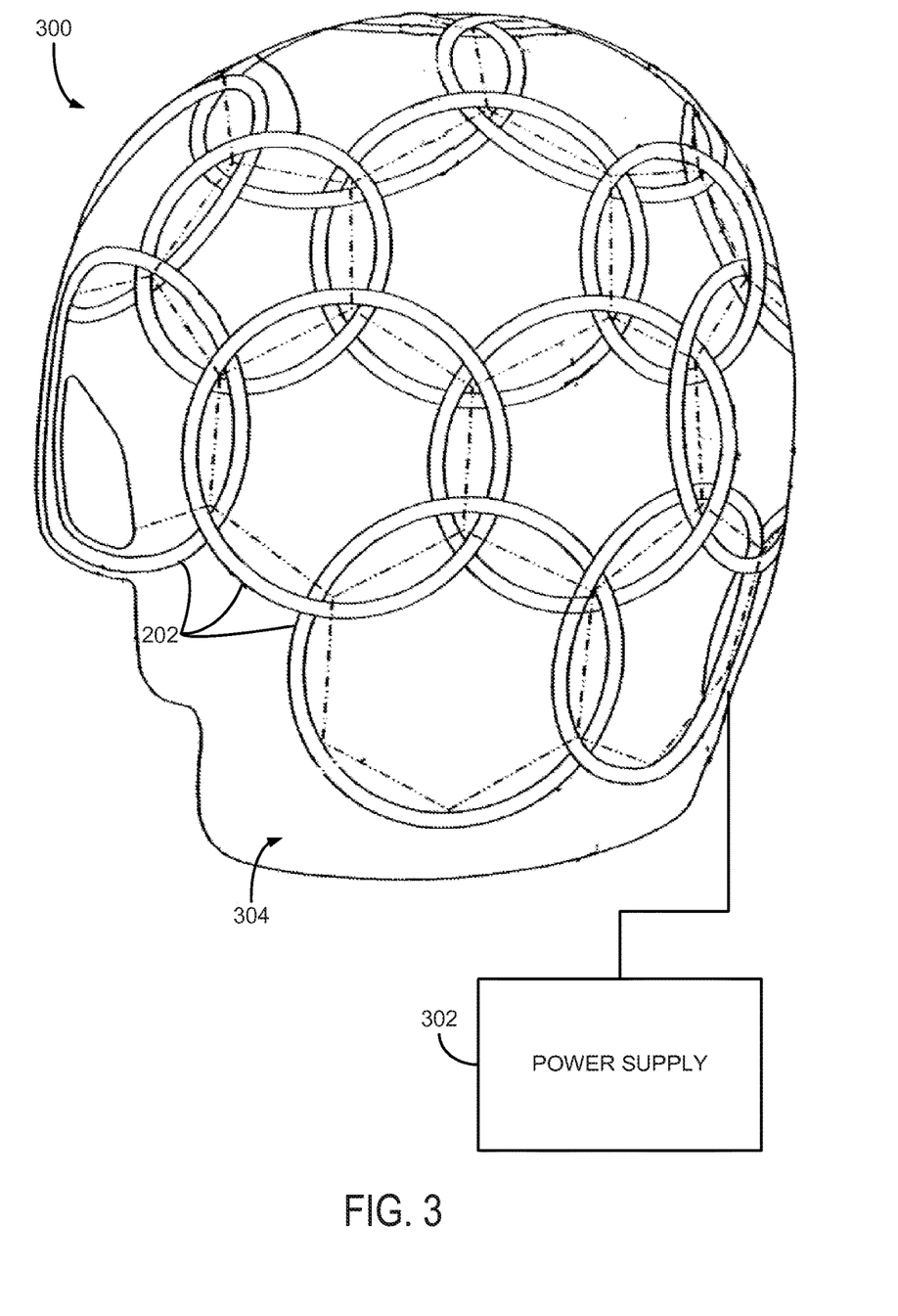
FIG. 3 is a schematic diagram of a coil system in accordance with the present invention formed as a head coil.

Referring to FIG. 3, an array 300 of the coil system described above with respect to FIG. 2 is illustrated. The array 300 may be coupled to a suitable power supply 302 chosen to supply up to, for example, 5 amps to each coil in the array 300. The power supply 302 must be designed to resist back-electromotive force (EMF) voltages induced in the loop coils of the array 300 during encoding gradient switching. For example, for an 10 cm loop lying 20 cm off isocenter and aligned in the X-Y plane, a gradient ramping through 40 mT/m in 100 microseconds may induce back-EMF of −0.5 Volts.

The coil array 300 may be mounted on a helmet or other housing or substrate system 304 and provide mechanical restraints to prevent coil motion due to torques during gradient switching in the scanner. Such restraints can be incorporated directly into the substrate 304. Regardless of the particular design, the mechanical restraints can be used to attach each coil to the substrate 304 to ensuring that coils 202 do not move due to torques that are produced on DC current carrying conductors when placed in the B0 field.

Referring to FIGS. 2 and 3, as described, in operation, the inductors 208, 210, 212 act as open circuits at RF or AC signals, but act as closed circuits permitting unencumbered flow of the DC signals. As such, the loops 202 produce B0 components in the X and Y planes, similar to the concomitant fields produced by physically-realizable gradient coils. However, since these components are small compared to the Z-component of the B0 and gradient fields, they do not substantially affect image quality.

While the greatest shimming performances is achieved using as many independent degrees of freedom as possible, it is possible to reduce hardware complexity by bridging adjacent RF coils with inductors selected to create a smaller basis set of shim coils whose shapes are tailored to generate the required field. The target-field method can be used to calculate current patterns for generating the desired shim field, such as described in Brideson M A, Forbes L K, Crozier S. Determining complicated winding patterns for shim coils using stream functions and the target-field method. Conc Magn Reson 14(1); 2002:9-18, which is incorporated herein by reference in its entirety. Ideal currents may be computed on a sphere surrounding the head. These currents can then be approximated by bridging RF coil traces in the appropriate locations. Alternatively, the measured inhomogeneity pattern in the body can be fit to the basis functions formed by the fields of the individual shim coils, which can be measured or modeled previously.

As illustrated in FIG. 3, arranging the coils 202 on a substrate 304 that tracks the contour of the head is advantageous. Specifically, close proximity of the shim coils to the head is advantageous. Each additional centimeter of air gap between the coils and the brain can degrade shim performance appreciably. By integrating the RF coils and shimming coils into the same physical space and using a substrate that contours the head, the present invention provides shim performance with simultaneous sensitivity that traditional systems cannot achieve. That is, by designing a system that integrates RF and shimming coils to share the same conductor, the shimming coils are as close as possible to the head without adversely impacting the performance of the RF coils.

Simulations show that 5 amps per coil is more than adequate to shim out sinus inhomogeneity in the human head even for 7 Tesla MRI. To test the ability of above-described, AC/DC coil array to shim out higher-order inhomogeneity in the brain, simulations were performed based on a traditional 32-channel RF coil array geometry. The Biot-Savart law was used to calculate the static field generated by a unit current in each loop. Representative field maps of human brain at 7 Tesla were then "shimmed" using the set of 32 simulated shim coil fields.

Shimming performance was simulated for 20 slices in the region of the brain displaying the worst B0 inhomogeneity in the brain. Optimal shim strength for the second-order shims was computed using a least-squares fit. For the multi-coil shim, a constrained optimization was performed in order to limit the shim current in each loop to less than 3 amps. Optimal shim weights were calculated both globally for the entire 20 slice volume as well as "dynamically" for each individual slice. When shim weights can be changed in between signal readouts, dynamic shimming allows the shim to be tailored to each acquired slice in multi-slice sequences.

Specifically, FIGS. 4A-4E illustrate the comparison of the above-described multi-coil system of the present invention and conventional second-order shimming for one of the slices with the most severe B0 inhomogeneity. FIG. 4A shows an initial field map and illustrates the inhomogeneities 400 of the field. Shimming of the inhomogeneities 400 of FIG. 4A is illustrated in FIG. 4B using global shimming and is illustrated in FIG. 4D using spherical harmonics up to second-order, which is the approach typically used in commercial MR scanners. As illustrated, substantial inhomogeneities 402, 404 still remain in FIGS. 4B and 4D, albeit, with the inhomogeneities 404 in FIG. 4D further shimmed when compared to the inhomogeneities 402 of FIG. 4B. However, FIGS. 4C and 4E clearly show that a 32-channel multi-coil shimming system, such as described above with respect to FIGS. 2 and 3, outperforms conventional shimming by further controlling inhomogeneities 406, 408. Specifically, FIG. 4C illustrates substantially controlled inhomogeneities 406, such as compared to the inhomogeneities 402, 404 of FIGS. 4B and 4D. This is particularly notable given that FIG. 4C illustrates performance when performing a global shim, yet the inhomogeneities in FIG. 4C are greatly reduced when compared the inhomgeneities 404 remaining when performing a traditional dynamic shimming. Further still, FIG. 4E shows that the inhomogeneities 408 can be even further controlled in a dynamic (slice-by-slice) shimming.

Figure 5A:
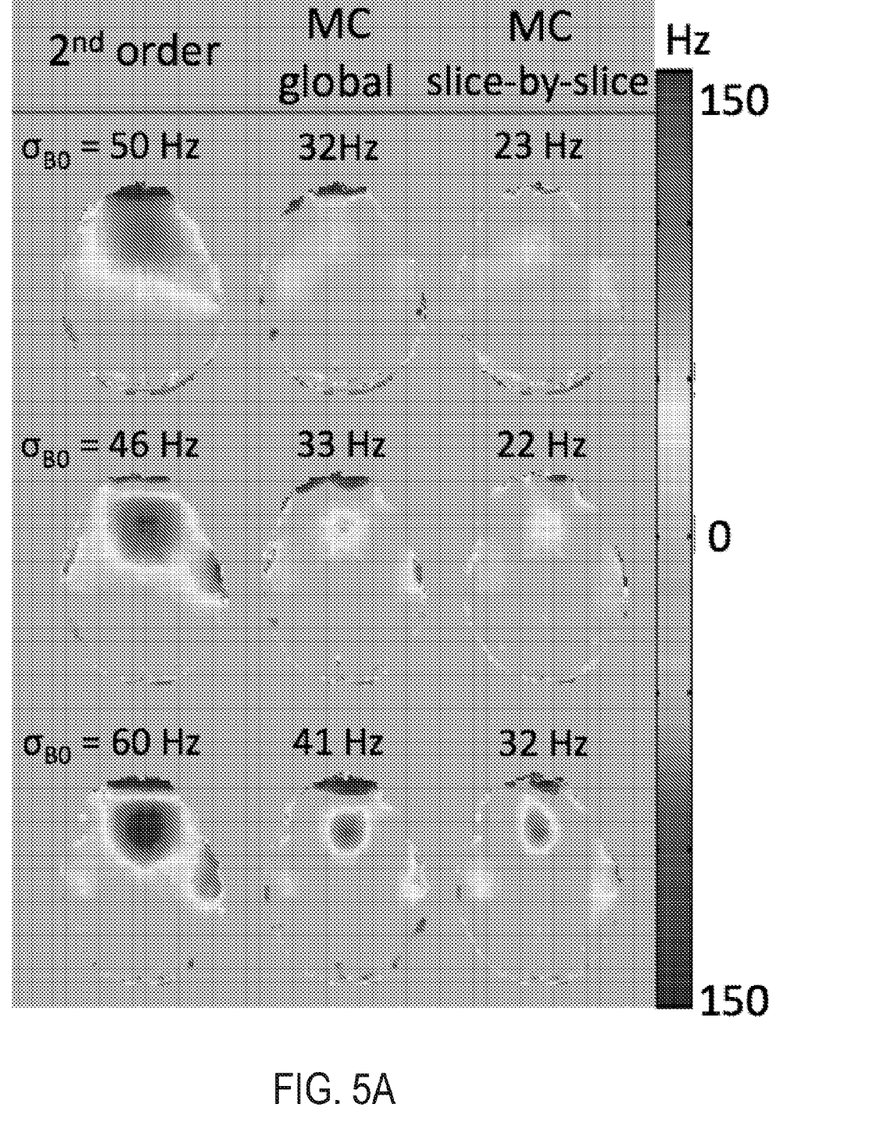
FIG. 5A is a comparison of a shimming simulation for 32ch shim-RF array in accordance with the present invention.

Referring to FIG. 5A, a comparison of a shimming simulation for 32ch shim-RF array (5 amps max) in accordance with the present invention is illustrated. Experimental B0 maps after 1st and 2nd order shimming were acquired and the shim currents calculated based on Biot-Savart field map models for the element geometry in accordance with the present invention. As illustrated, the present invention provides substantial shimming and sensitivity.

In some settings it is possible to further improve shimming efficiency and reduce peak currents by using multiple closely stacked loops or loops with multiple turns to boost the inductance. The DC path can then be bridged between coils with inductive chokes. All of the coils may be capacitively coupled together so that each of them contributes signal for RF reception. In this way, the shimming performance per amp of current is improved without substantially adverse impact on the RF SNR.

Figure 5B:
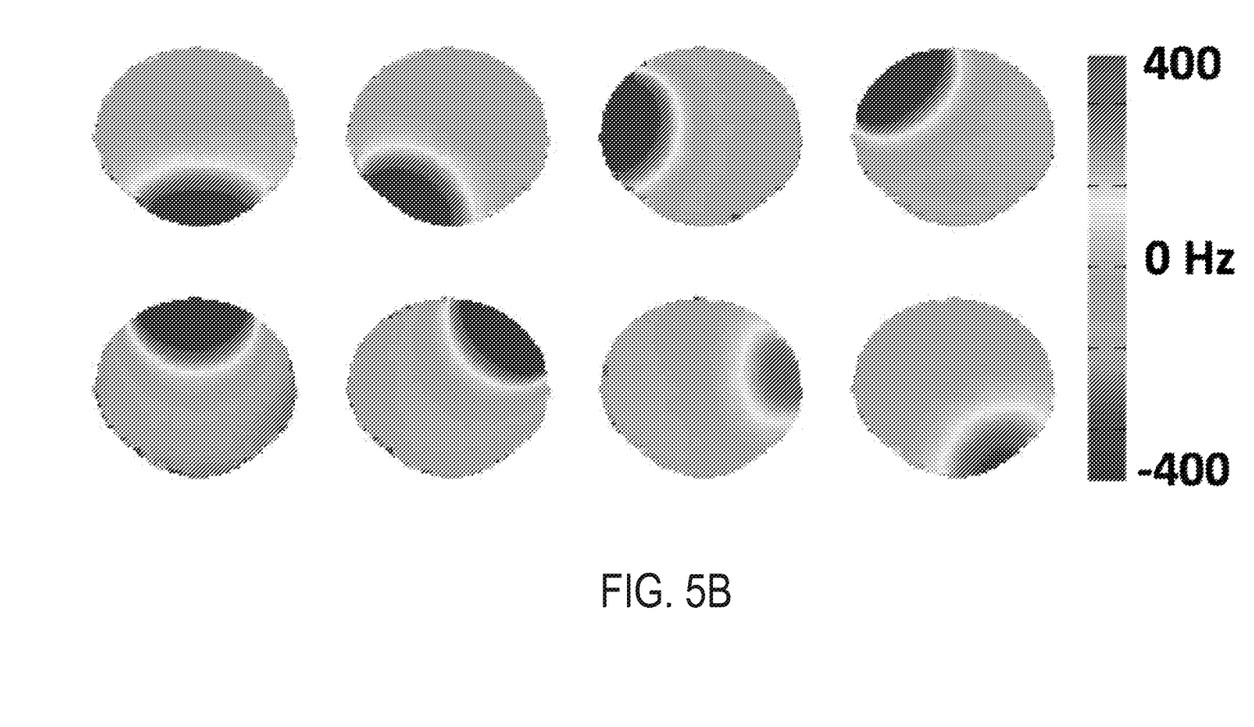
FIG. 5B is an example of field maps for 8 representative coils of a 32 channel coil designed in accordance with the present invention.

Referring to FIG. 5B, an example of field maps acquired using the present invention designed as a 32 channel coil are provided. In particular, the images illustrate transverse field maps acquired in phantom for eight representative shim coils at the mid-plane of the helmet with 1 A of test current flowing (240 mm field of view). The maps demonstrate the circumferential spatial degrees of freedom provided by the shim array for compensating B0 inhomogeneity. That is, these images demonstrate how the B0 shim fields generated by the coils vary circumferentially around the body.

Figure 4:
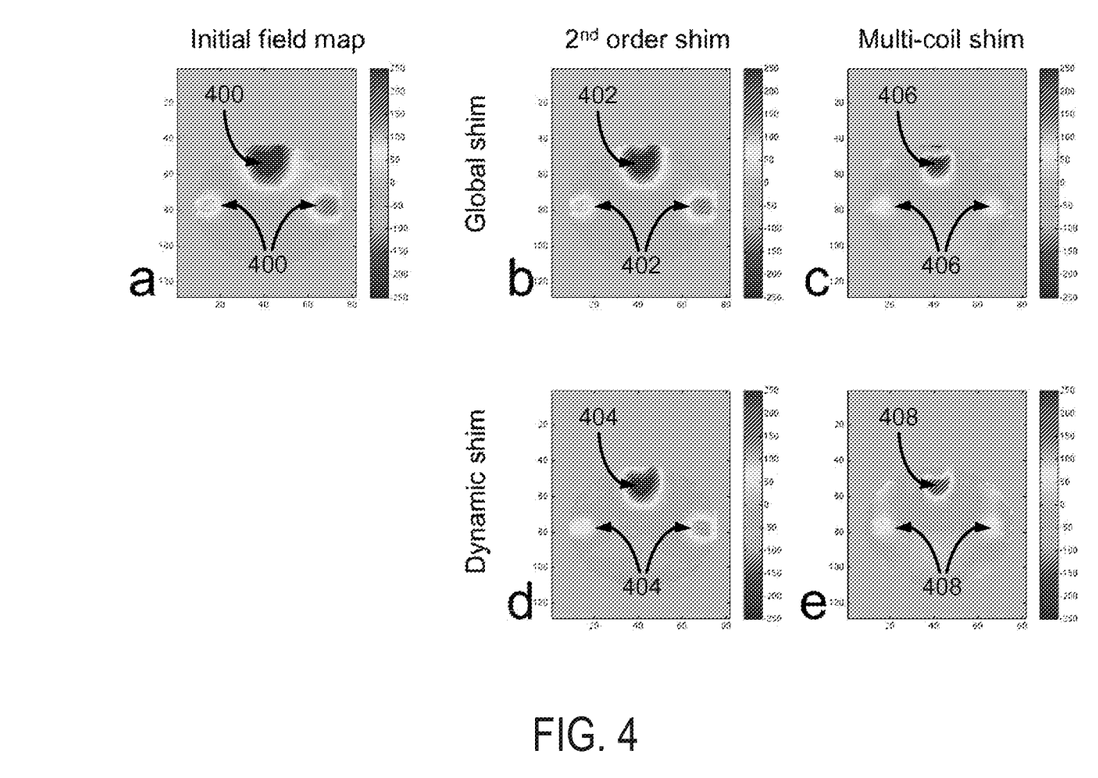
FIGS. 4a-4e are graphs showing the effectiveness of traditional shimming techniques and the shimming techniques of the present invention.
Figure 6:
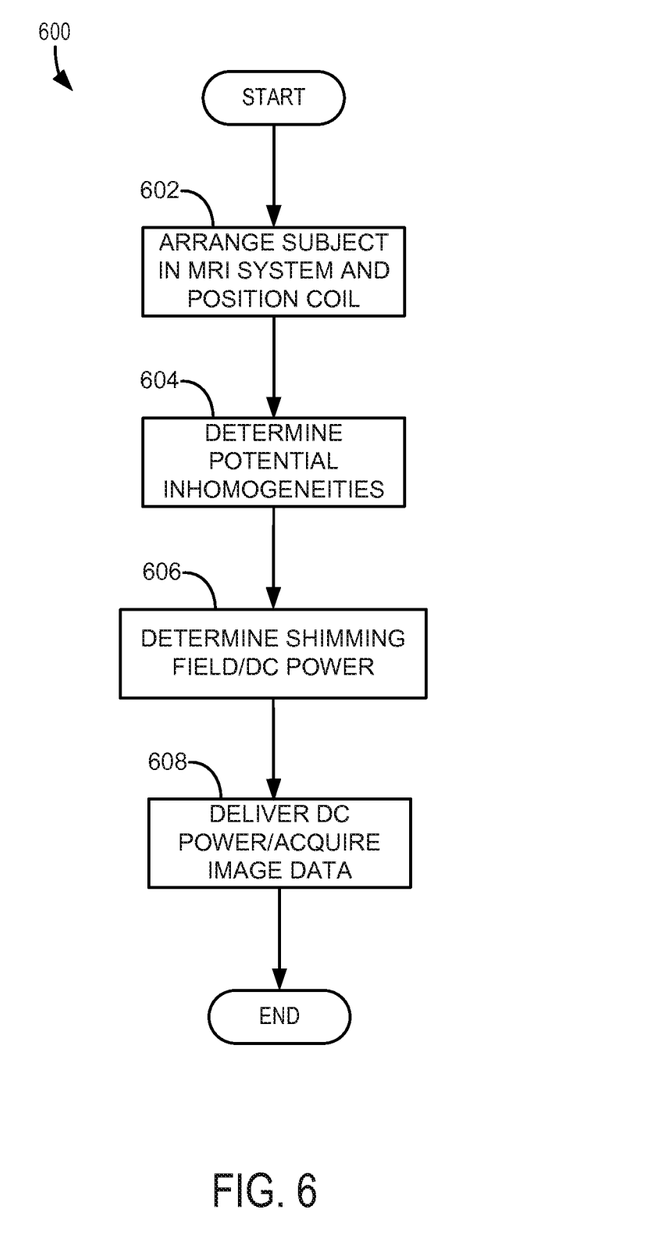
FIG. 6 is a flow chart setting forth exemplary steps of a method in accordance with the present invention.

Referring to FIG. 6, a process 600 in accordance with the present invention includes, at process block 602, arranging the subject to be imaged in the MRI system and positioning an RF coil, such as described above, proximate to the desired ROI. The coil, as described above, is connected to the MRI system to communicate RF excitation signals and/or medical imaging signals received during the imaging process and is connected to a power source to receive DC power. As described above with respect to FIG. 4, at process block 604, potential magnetic field inhomogeneities may be determined. It is contemplated that the potential magnetic field inhomogeneities may be determined for each individual imaging process or may known or anticipated magnetic field inhomogeneities. Regardless of how the magnetic field inhomogeneities are determined, at process bock 606, a desired shimming field is determined and DC power characteristics to create a shimming field using the RF coil are determined. At process block 608, DC power is delivered to the RF coil to generate the desired shimming field, and RF transmit and receive processes are performed to acquire image data from the subject using the RF coil.

Notably, the coil system of the present invention can be used to create frequency isocontours enabling excitation of regions of interest within the object or the dephasing of signal from unwanted regions. This provides an alternative to multidimensional shape-selective RF pulses, which tend to be long and have high levels of RF power deposition, and parallel transmit arrays, which involve considerable hardware and software complexity. Thus, the switchable shim coil array in accordance with the present invention provide a powerful tool for exciting regions of interest and improving flip angle homogeneity at ultra high field.

The present invention is particularly advantageous when shimming the frontal and temporal lobes in the human head. B0 inhomogeneity in these regions is one of the primary obstacles to routine measurement of the blood oxygen-level dependent (BOLD) response in functional MRI (fMRI) scans at 7 Tesla. Commercial MRI scanners are not equipped with shim coils capable of generating the higher-order harmonics necessary to shim these localized regions of inhomogeneity. The present invention substantially improves upon traditional multi-coil shimming approaches for the human head by integrating it with an RF receive array, permitting the most efficient possible use of space and materials in the magnet bore near the patient's head. More generally, as the clinical base continues to move to higher and higher B0 field strength, where shimming becomes more important (since susceptibility artifacts increase), the present invention solves many clinical problems.

Many other imaging applications also benefit from our approach, such as imaging of the neck, brain stem, and cervical spine. B0 homogeneity in the spine suffers from discontinuities (such as between the shoulders and air) that distort the B0 field lines and cause pronounced image artifacts. Abdominal imaging also suffers regions of reduced B0 uniformity near air and gas pockets. Commercial MRI scanners are not equipped with a flexible shimming system capable of correcting this B0 inhomogeneity. Integrating shimming and RF signal reception into a close-fitting spine coil array, such as provided in the present invention, provides an ideal way to maximize SNR while also eliminating shim-induced image artifacts.

The coil system of the present invention can be used as a dual-purpose shimming/signal detection device because the DC and RF currents do not interfere with one another or degrade one another's performance. The present invention allows both the RF loops and the shim loops to occupy their preferred location, close to the body, without one interfering with the other because RF and shim loops utilize the same loops. The present invention improves the efficiency of the shim coils and their spatial frequency content (allowing to potentially shim-out higher order spatial variations) by moving the shim loops closer to the body than previous shim array configurations that are separate from the RF loops. By using a helmet-type geometry for the shim coils, the shim coil array produces more significant field components in the z direction, which is the direction needed for shimming compared to loops arranged on a cylinder, where the axis of the cylinder is the z axis, further increasing their efficiency.

The present invention permits independent control of the RF and DC currents. For larger arrays of coils, such as 64-channel RF arrays, the advantages of multi-coil shimming of the present invention is even greater than the more-common 32-channel RF arrays. The AC/DC arrays of the present invention can also be used for other body regions beyond the head.

Dramatically improved shimming with an AC/DC array benefits virtually all MRI pulse sequences, but the benefits are particularly pronounced in sequences such as echo planar imaging (EPI) and susceptibility weighted imaging (SWI). EPI sequences suffer signal loss and geometric distortion in the vicinity of B0 inhomogeneity. This limits the performance of functional MRI scans of the brain, particularly in areas such as the frontal lobe that suffer from sinus-induced B0 distortions. The AC/DC array improves the quality of SWI, an approach that is sensitive to changes in phase caused by B0 inhomogeneity. The applications of SWI include detection of iron-containing lesions in patients with multiple sclerosis and others.

As compared with conventional multi-coil shim coils, the single-turn RF/shim loops of the present invention present greatly reduced inductance by at least an order of magnitude, permitting them to be switched more quickly for dynamic shimming applications. Also, as noted, the RF coils are already inductively decoupled from their neighbors and, because inductive decoupling is broadband, this controls coupling between adjacent RF/shim coils during dynamic shimming. Furthermore, the RF/shim coils exploit the fields naturally generated by loop coils in the body. In the magnetostatic approximation, the field can be decomposed into components transverse to the polarizing B0 field and components aligned with B0 filed. The field components oriented transverse to B0 filed can be used for signal reception (B1− field) or signal excitation (the B1+ field) if they alternate at the resonant frequency of the spins (the Larmor frequency) while the component aligned with B0 filed can be used for shimming. This natural synergy further strengthens the case for using the same conducting loop for both B0 shimming and RF signal detection as provided by the present invention.

The present invention has been described in terms of one or more embodiments, and it should be appreciated that many equivalents, alternatives, variations, and modifications, aside from those expressly stated, are possible and within the scope of the invention.

The invention claimed is:

1. A coil system configured to be utilized with a magnetic resonance imaging (MRI) system to acquire medical imaging data from a subject during a medical imaging procedure, the system comprising:
a conductive loop configured to be arranged proximate to a region of interest (ROI) of the subject during the medical imaging procedure;
an alternating current (AC) circuit electrically connecting the conductive loop to an AC electrical connection configured to be coupled to the MRI system to communicate medical imaging signals received by the conductive loop from the ROI during the medical imaging procedure to the MRI system;
a direct current (DC) circuit electrically connecting the conductive loop to a DC electrical connection configured to be coupled to a DC power source; and
a plurality of circuit components connected to the conductive loop and configured to block DC signals from reaching the AC electrical connection.

2. The coil system of claim 1 wherein the plurality of circuit components include blocking capacitors to block DC coupled currents from accessing the AC electrical connection.

3. The coil system of claim 1 further comprising another plurality of circuit components including inductors and LC filtering circuits configured to block AC signals from reaching the DC electrical connection.

4. The coil system of claim 3 wherein the another plurality of circuit components include inductors coupled between the AC electrical connection and the DC electrical connection.

5. The coil system of claim 1 further comprising a plurality of conductive loops and respective AC circuits and DC circuits forming a coil array.

6. The coil system of claim 5 further comprising a substrate having mounted thereon the plurality of conductive loops to arrange the plurality of conductive loops about the ROI.

7. The coil system of claim 6 wherein the substrate is configured to form a helmet and the ROI is within a head of the subject.

8. A magnetic resonance imaging (MRI) system, comprising:
a magnet system configured to generate a static magnetic field about at least a region of interest (ROI) of a subject arranged in the MRI system;
a plurality of gradient coils configured to establish at least one magnetic gradient field with respect to the static magnetic field;
a radio frequency (RF) system comprising:
an RF signal input configured to deliver medical imaging signals acquired by the RF system during a medical imaging process conducted with the subject to the MRI system;
an RF antenna shaped to be arranged proximate to the ROI of the subject;
an alternating current (AC) circuit electrically connecting the RF antenna to the RF signal input to communicate the medical imaging signals received by the RF antenna from the ROI during the medical imaging process to the MRI system;
a direct current (DC) circuit electrically connecting the RF antenna to a DC electrical connection;
a power source coupled to the DC electrical connection of the DC circuit to deliver DC power to the RF antenna to generate a shimming magnetic field using the RF antenna to compensate for inhomogeneities of the static magnetic field generated by the magnet system.

9. The MRI system of claim 8 wherein the RF system further includes a plurality of circuit components connected to the RF antenna and configured to at least one of block DC signals from reaching the AC electrical connection and block AC signals from reaching the DC electrical connection.

10. The MRI system of 9 wherein the plurality of circuit components includes at least one of blocking capacitors coupled between the AC electrical connection and the DC electrical connection and inductors coupled between the AC electrical connection and the DC electrical connection.

11. The MRI system of claim 8 wherein the RF system further includes a plurality of RF antennae and respective AC circuits and DC circuits forming a coil array.

12. The MRI system of claim 11 wherein RF system includes on a substrate having mounted thereon the plurality of RF antennae to arrange the plurality of RF antennae about the ROI.

13. The MRI system of claim 12 wherein the substrate is configured to form a helmet and the ROI is within a head of the subject.

14. A method for performing a medical imaging procedure using a magnetic resonance imaging (MRI) system, the method comprising:
arranging a subject within the MRI system;
positioning external imaging coils to acquire image data from the subject using at least one RF antenna;
coupling the at least one RF antenna to an RF input of the MRI system to deliver the image data to the MRI system;
coupling the at least one RF antenna to a direct current (DC) power source;
determining a position of magnetic field inhomogeneities in a static magnetic field of the MRI system with respect to the subject;
determining a shimming field configured to compensate for the magnetic field inhomogeneities;
delivering a DC power from the DC power source to the at least one RF antenna configured to at least partially compensate for the magnetic field inhomogeneities;
acquiring image data form the subject using the at least one RF antenna while at least partially compensating for the magnetic field inhomogeneities using the RF antenna.

15. The method of claim 14 further comprising blocking DC signals from reaching the RF input.

16. The method of claim 14 further comprising blocking image data from the DC power source.

17. The method of claim 14 wherein the image data is acquired from RF signals corresponding to a blood oxygen-level dependent (BOLD) response in the subject during an functional MRI (fMRI) imaging process.

18. The method of claim 14 wherein the magnetic field inhomogeneities are induced by discontinuities between tissue and air within the subject.

19. The method of claim 14 wherein the external imaging coils are positioned in an array that contours the head of the subject.

* * * * *